United States Patent [19]

Sugo et al.

[11] Patent Number: 5,709,212

[45] Date of Patent: Jan. 20, 1998

[54] BLOOD PRESSURE MEASURING APPARATUS

[75] Inventors: Yoshihiro Sugo; Takeshi Sohma, both of Tokyo, Japan

[73] Assignee: Nihon Kohden Corporation, Tokyo, Japan

[21] Appl. No.: 413,223

[22] Filed: Mar. 30, 1995

[30] Foreign Application Priority Data

Mar. 30, 1994 [JP] Japan ................................ 6-061550

[51] Int. Cl.$^6$ ........................................ A61B 5/00
[52] U.S. Cl. ........................ 128/681; 128/682; 128/687
[58] Field of Search ............................ 128/672, 677, 128/680–7

[56] References Cited

U.S. PATENT DOCUMENTS

| | | | |
|---|---|---|---|
| 4,907,596 | 3/1990 | Schmid et al. | 128/672 |
| 5,237,997 | 8/1993 | Greubel et al. | 128/672 |
| 5,564,427 | 10/1996 | Aso et al. | 128/681 |
| 5,603,329 | 2/1997 | Hosaka et al. | 128/680 |

*Primary Examiner*—Robert L. Nasser
*Attorney, Agent, or Firm*—Sughrue, Mion, Zinn, Macpeak & Seas, PLLC

[57] ABSTRACT

A blood pressure measuring device includes: a memory for storing a standard constant α; an input means for inputting a correcting blood pressure value; a time interval reference point detection section for detecting a time interval detection reference point in a pulse wave on the side of aortae; a pulse wave detection section for detecting a pulse wave on the side of peripheral blood vessels appearing with a time lag with respect to the pulse wave on the side of aortae; a pulse wave propagation time measurement section for measuring a pulse wave propagation time based on respective detected outputs from the time interval detection reference point detection means and the pulse wave detection means; an operation means for determining a constant β using the blood pressure value for calibration, pulse wave propagation time, and standard constant α inputted for calibration; an operation means for calculating the blood pressure value from the pulse wave propagation time measured at a predetermined time interval for measuring a circadian blood pressure fluctuation, and the standard constants α, β; a memory for consecutively storing the measured pulse wave propagation time and the blood pressure value calculated from the pulse wave propagation time; and an external output connector for outputting at least the blood pressure value and pulse wave propagation time data as a result of the circadian blood pressure fluctuation measurement.

6 Claims, 3 Drawing Sheets

BLOOD PRESSURE MEASURING APPARATUS

BACKGROUND OF THE INVENTION

1. Field of the Invention

The invention relates to a Holter type blood pressure measuring apparatus for measuring circadian blood pressure fluctuation and, more particularly, to a blood pressure measuring apparatus for measuring blood pressure based on pulse wave propagation time.

2. Related Art

As a noninvasive Holter type blood pressure measuring device for measuring circadian blood pressure fluctuation, a blood pressure measuring device using a cuff has heretofore been known.

This blood pressure measuring device requires that the cuff be wrapped around the upper part of an arm of a subject, and this has imposed various problems. That is, the weight of the cuff is annoying to the subject; the wrapped cuff binds the daily life of the subject; the subject feels uncomfortable during night with the cuff wrapped; and the subject may suffer from somnipathy due to cuff driving noise and the like. In addition, the cuff has an artifact caused by a shock.

A blood pressure measuring device that measures blood pressure utilizing pulse wave propagation speed (the time required for a pulse wave to be propagated a predetermined distance) is known as a noninvasive blood pressure measuring device that has overcome these problems encountered by the aforementioned blood pressure measuring device using the cuff.

The principle of blood pressure measurement from the pulse wave propagation speed can be explained in the following way.

The pulse wave propagation time will be described first. As shown in FIG. 3, a specific point of a pulse wave on the side of peripheral blood vessels such as a finger or an ear appears with a time lag with respect to a specific point of an aortic pulse wave. This time lag is the pulse wave propagation time.

The pulse wave propagation speed corresponding to the time required for a pulse wave to be propagated a predetermined distance is expressed in the form of a function of the modulus of volumetric elasticity of a blood vessel. When the blood pressure increases, the modulus of volumetric elasticity of the blood vessel is increased; the blood vessel wall hardens; and the propagation speed is increased. Therefore, a blood pressure fluctuation can be found from the pulse wave propagation speed.

The blood pressure measuring device utilizing the pulse wave propagation time measures blood pressure by using a cuff or the like and must make a calibration with reference to the measured blood pressure data.

For the calibration, blood pressures and pulse wave propagation times are measured when a subject is at rest and when the subject is in movement.

Here, let it be assumed that the blood pressure and the pulse wave propagation time when the subject is at rest are P1, T1; the blood pressure and the pulse wave propagation time when the subject is in movement are P2, T2; and constants inherent in the subject are $\alpha$, $\beta$. Then, the blood pressures P1, P2 are given as $P1 = \alpha T1 + \beta$ $P2 = \alpha T2 + \beta$ Therefore, by measuring P1, T1, P2, T2, the constants $\alpha$, $\beta$ can be calculated from the above two equations. Once the constants $\alpha$, $\beta$ have been calculated, the blood pressure of the subject can be measured only by measuring the pulse wave propagation time from then on.

By the way, it is essential for the noninvasive blood pressure measuring method using the cuff to make calibration to determine the inherent constants $\alpha$, $\beta$, and this calibration not only bothers the subject but also entails much time.

SUMMARY OF THE INVENTION

The invention has been proposed to overcome such problems encountered by the conventional art. Accordingly, the object of the invention is to provide a Holter type blood pressure measuring device that measures blood pressure using the pulse wave propagation time without entailing much time in the calibrating operation to determine the inherent constants $\alpha$, $\beta$ nor burdening the subject.

To achieve the above object, the invention is applied to a blood pressure measuring device that includes: a memory for storing a standard constant $\alpha$ by which a pulse wave propagation time is multiplied in calculating a blood pressure value from the pulse wave propagation time; an input means for inputting a blood pressure value for calibration; a time interval detection reference point detection means for detecting a time interval detection reference point in a pulse wave on the side of aortae of a living organism; a pulse wave detection means for detecting a pulse wave on the side of peripheral blood vessels appearing with a time lag with respect to the pulse wave on the side of aortae; a pulse wave propagation time measurement section for measuring a pulse wave propagation time based on respective detected outputs from the time interval detection reference point detection means and the pulse wave detection means; a first operation means for determining a constant $\beta$ to be added in calculating the blood pressure value from the pulse wave propagation time using the inputted blood pressure value for calibration, a single pulse wave propagation time measured for calibration, and the prestored standard constant $\alpha$; a second operation means for calculating the blood pressure value from the pulse wave propagation time measured at a predetermined time interval for measuring a circadian blood pressure fluctuation, the standard constant $\alpha$, and the already determined constant $\beta$; a memory for consecutively storing the measured pulse wave propagation time and the blood pressure value calculated from the pulse wave propagation time; and an output means for outputting at least the blood pressure value and pulse wave propagation time data stored in the memory as a result of the circadian blood pressure fluctuation measurement.

According to the aforementioned construction, the constant $\beta$ inherent in a subject can be determined by a single round of blood pressure measurement by presetting and storing the standard constant $\alpha$ in memory. This can dispense with cumbersome calibration for determining the constants $\alpha$, $\beta$.

Once the inherent constant $\beta$ has been determined, blood pressure values can be calculated using pulse wave propagation times and the constants $\alpha$, $\beta$ by measuring the pulse wave propagation times at a predetermined cycle. Therefore, the circadian blood pressure fluctuation can be measured.

Thereafter, if it is judged necessary to measure blood pressure more accurately after having diagnosed the measured data, then a calibration is made to determine the constants $\alpha$, $\beta$ again, so that more accurate measurement results can be obtained. In this case, the pulse wave propagation time data can be reused.

DETAILED DESCRIPTION OF THE PREFERRED EMBODIMENT

An embodiment of the invention will now be described in detail with reference to the drawings.

Figure 1:
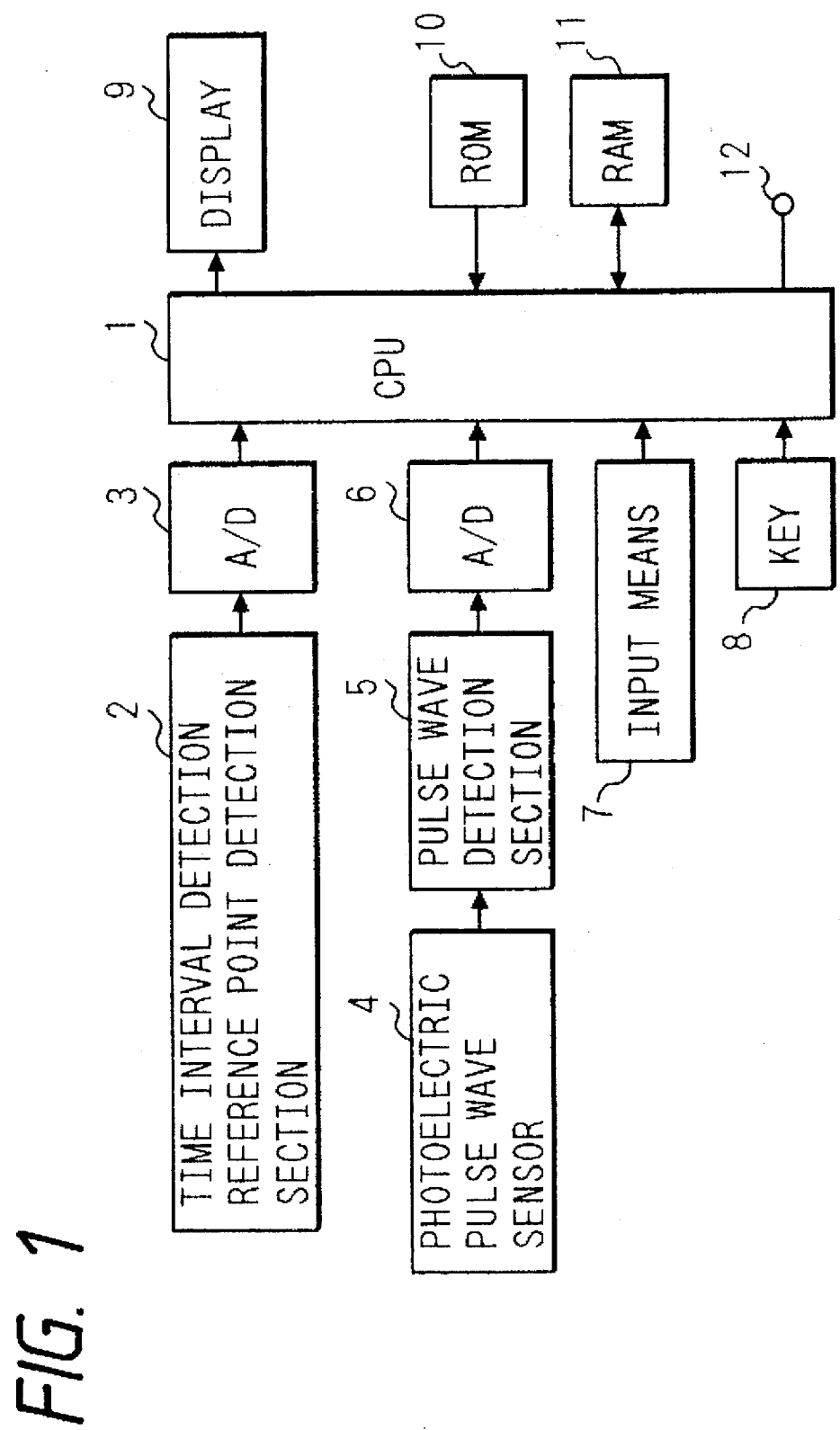
FIG. 1 a block diagram showing a blood pressure measuring device, which is an embodiment of the invention.

FIG. 1 shows a blood pressure measuring device, which is an embodiment of the invention in the form of a block diagram. In FIG. 1, a time interval detection reference point detection section 2 is designed to detect a timing at which the aortic pressure hits the bottom value substantially simultaneously with the generation of an R wave in an electrocardiogram. The output of this detection section 2 is converted into a digital signal by an A/D converter 3, and inputted to a CPU (Central Processing Unit) 1. The time interval detection reference point detection section 2 may include an electrode attached to the chest of a subject, and an electrocardiographic R wave detection section to which the electrode is connected. Further, the time interval detection reference point detection section 2 may, instead, include a photoelectric pulse wave sensor or pressure pulse wave sensor for detecting an aortic pulse wave, and a pulse wave detection section to which either one of these sensors is connected.

A photoelectric pulse wave sensor 4 is attached to, e.g., a finger of a subject to measure the pulse wave on the side of peripheral blood vessels. The output of this sensor 4 is applied to the pulse wave detection section 5, so that the pulse wave at the position of the subject to which the sensor 4 is attached can be detected. The output of the pulse wave detection section 5 is inputted to the CPU 1 after it is converted into a digital signal by an A/D converter 6.

A key 8 is pressed for calibration to determine a constant β inherent in the subject.

From an input means 7, not only a standard constant α and a blood pressure value for calibration $P_0$ are inputted but also a measuring time interval for measuring circadian blood pressure fluctuation is set. Further, it is also from the input means 7 that a command for starting a circadian blood pressure fluctuation measurement is inputted and that a command for outputting measured data can be given.

The CPU 1 executes a processing program based on signals inputted from the A/D converters 3, 6, the key 8, and the input means 7 for such control as to display the processing results on a display 9 and output the measured data to an external output connector 12. A memory (ROM) 10 that is connected to the CPU 1 stores the processing program, and a memory (RAM) 11 that is also connected to the CPU 1 stores in-process data.

It may be noted that the CPU 1 constitutes the pulse wave propagation time measurement section, and the first and second operation means in claim 1.

Figure 2:
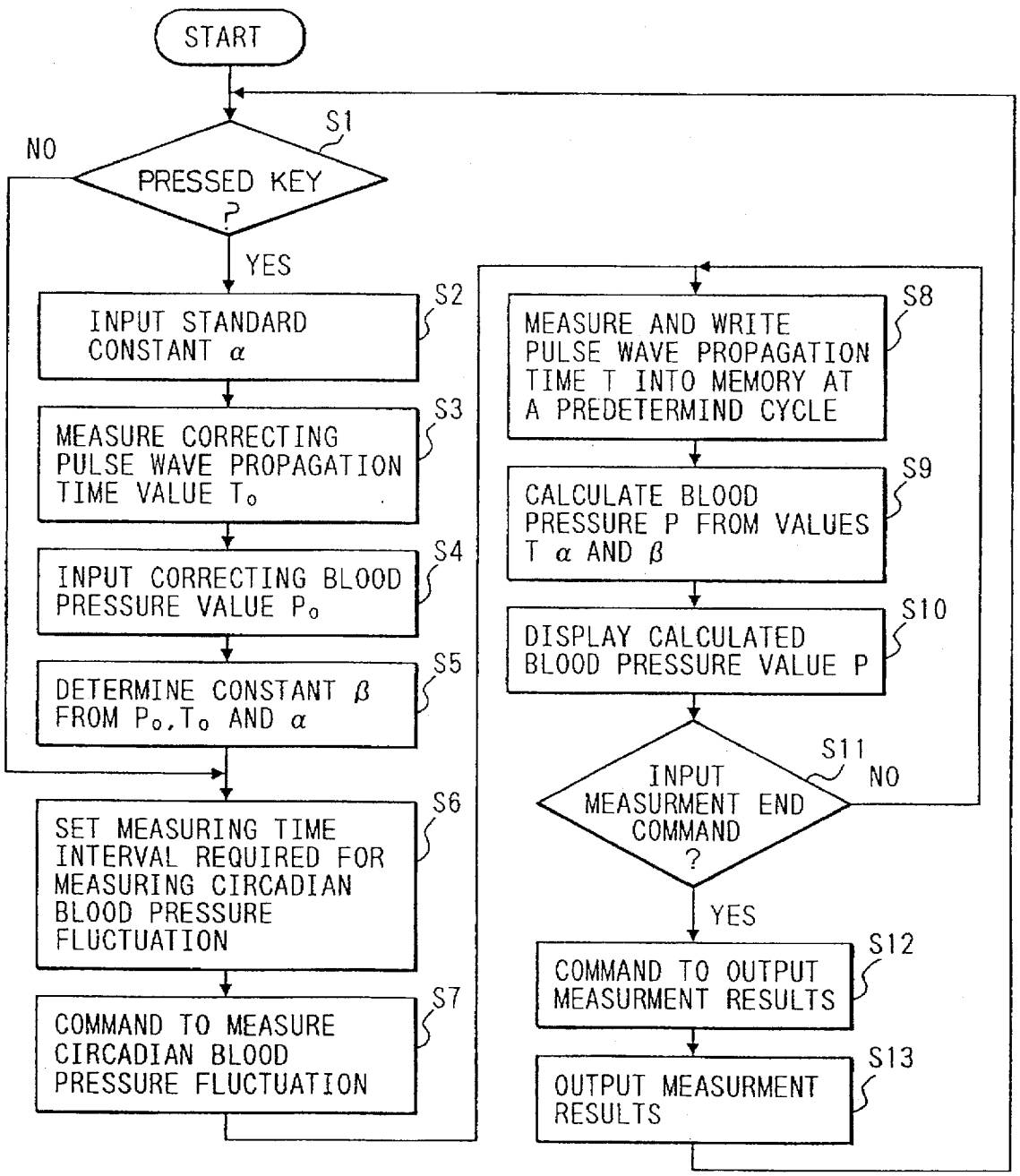
FIG. 2 a flowchart showing the procedure of a series of processing to be executed by the blood pressure measuring device of FIG. 1.
Figure 3:
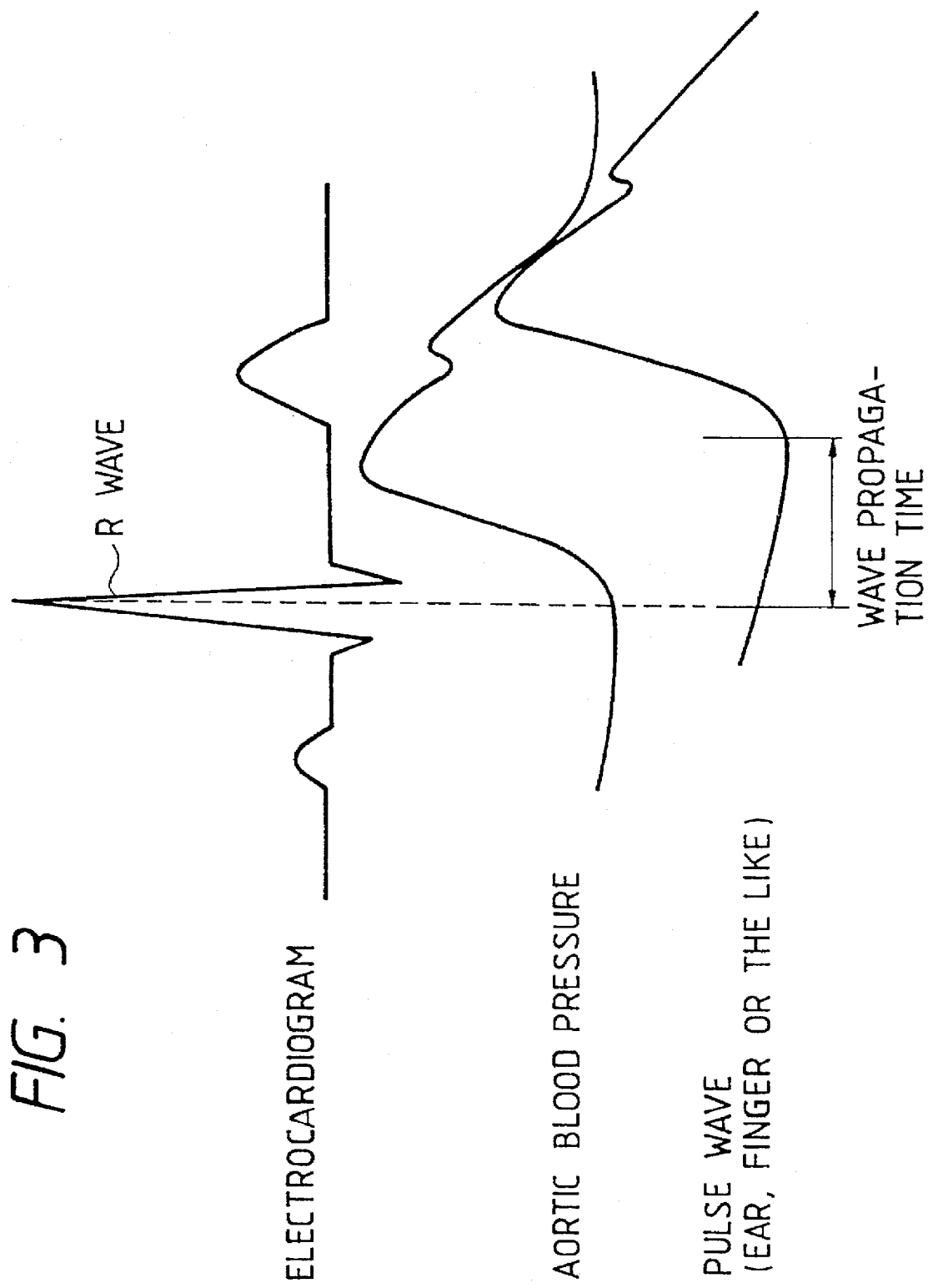
FIG. 3 is a waveform diagram illustrative of a pulse wave propagation time.

An operation of the thus constructed blood pressure measuring device will be described with reference to a flowchart shown in FIG. 2.

First, whether or not the key 8 has been pressed is judged in Step S1.

After the key 8 has been pressed in Step S1, the standard constant α, which serves as a proportional constant for the pulse wave propagation time in calculating a blood pressure value from a pulse wave propagation time is inputted from the input means 7 as a calibrating parameter in Step S2. The inputted standard constant α is written to the memory 11.

Then, in Step S3, data inputted from the A/D converters 3, 6 are processed by the CPU 1 to measure a correcting pulse wave propagation time $T_0$. The obtained pulse wave propagation time value $T_0$ is written to the memory 11.

Then, in Step S4, a separately prepared blood pressure measuring device with a cuff is used to measure a blood pressure value $P_0$ immediately after the pulse wave propagation time $T_0$ has been measured, and the measured blood pressure value $P_0$ is inputted as the blood pressure value for calibration $P_0$ from the input means 7. The obtained blood pressure value $P_0$ is written to the memory 11.

Then, in Step S5, the values $P_0$, $T_0$, and α read from the memory 11 are processed by the CPU 1, so that the constant β (correcting parameter) is determined based on the following equation. The determined constant β is written to the memory 11.

$P_0 = \alpha T_0 + \beta$ $\beta = P_0 - \alpha T_0$

Then, in Step S6, a measuring time interval (measuring cycle) required for measuring the circadian blood pressure fluctuation is set from the input means 7. It may he noted that the measuring time interval is set to, e.g., 1 minute. The set measuring time interval is written to the memory 11.

Then, in Step S7, a command for measuring the circadian blood pressure fluctuation is inputted from the input means 7.

The CPU 1 that has received the command processes the data from the A/D converters 3, 6 at a predetermined cycle stored in the memory 11 to measure a pulse wave propagation time T, and writes the measured value to the memory 11 in Step S8.

Then, the CPU 1 processes the values T, α, β read from the memory 11 to calculate a blood pressure value P based on the following equation in Step S9.

$P = T\alpha + \beta$

The calculated blood pressure value P is not only written to the memory 11 but also displayed on the display 9 in Step S10.

The processing from Step S8 to Step S10 is repeated at a predetermined time interval until a measurement end command is given in Step S11.

After the measurement end command has been inputted from the input means 7 in Step S11 and the circadian blood pressure fluctuation measurement has been ended as the Holter type blood pressure measuring device, the CPU 1, upon reception of a command for outputting measurement results from the input means 7 in Step S12, outputs from the external output connector 12 the blood pressure values P and the pulse wave propagation times T, which are the data measured at a predetermined time interval, and the constants α, β, which are the correcting parameters, in Step S13. These values are all stored in the memory 11.

Thereafter, returning to Step S1, the circadian blood pressure fluctuation measurement can be made on the same subject repetitively based on a series of processing from Step S6 to Step S13 using the same constants α, β unless the key is pressed.

If it is judged from the result of a diagnosis made on the basis of the outputted measured data (the blood pressure value P and pulse wave propagation time T data) and a blood pressure fluctuation pattern that it is necessary to make a more accurate blood pressure diagnosis, then the constants α, β, which are the parameters, are re-calibrated by carrying out a movement test or the like.

In this case, after the constant β has been determined from the re-calibrated constant α, the already outputted measured pulse wave propagation time T data are reused. That is, more accurate blood pressure values P can be re-determined by using such pulse wave propagation time T data and re-calibrated parameters α, β.

It may be noted that the operation of measuring the circadian blood pressure fluctuation of a subject can be repeated based on a series of processing from Step S3 after pressing the key in Step S1 and then inputting a re-calibrated constant α again in Step S2.

According to the blood pressure measuring device as exemplified in this embodiment, it is not necessary to take time and correct the constants α, β for circadian blood pressure measurements not requiring accuracy, but the circadian blood pressure fluctuation can be measured by determining the constant β using the standard constant α, which in turn contributes to reducing burdens borne by the subject noticeably.

If the standard constant α is stored in the memory (ROM) 10 beforehand, the operation of storing the standard constant α from an external device in Step S2 may be dispensed with.

As described in the foregoing, the invention is characterized as prestoring a standard constant α for measuring the circadian blood pressure fluctuation. Therefore, the advantage that the constant β can be determined by a single round of blood pressure measurement can be provided. Blood pressure values can thereafter be calculated consecutively from measured pulse wave propagation time data by measuring pulse wave propagation times at a predetermined cycle.

Further, if it is judged from the measured blood pressure and pulse wave propagation time data as well as from the blood pressure fluctuation pattern that a more accurate blood pressure diagnosis is necessary, then highly accurate blood pressure values can be determined by using the constants α, β re-calibrated by a movement test or the like and reusing the measured pulse wave propagation time data.

As described above, the invention is designed to dispense with the time and labor required for making a calibration for those circadian blood pressure fluctuation measurements not requiring accuracy. Therefore, the invention can provide the advantage that not only burdens on the part of the subject as well as on the medical staff can be reduced significantly but also the overall examination time can be shortened. In addition, the invention is designed to reuse the pulse propagation time data. Therefore, the advantage that the measured data can be utilized effectively can be provided.

What is claimed is:

1. A blood pressure measuring apparatus comprising:

a memory for storing a constant α by which a pulse wave propagation time is multiplied in calculating a blood pressure value from the pulse wave propagation time;

input means for inputting a blood pressure value for calibration;

time interval detection reference point detecting means for detecting a time interval detection reference point in a pulse wave on a side of an aortae of a living organism;

pulse wave detection means for detecting a pulse wave on a side of peripheral blood vessels appearing with a time lag with respect to the pulse wave on the side of the aortae;

pulse wave propagation time measurement section for measuring a pulse wave propagation time based on respective detected outputs from the time interval detection reference point detection means and the pulse wave detection means;

first operation means for determining a constant β to be added in calculating the blood pressure value from the pulse wave propagation time using the inputted calibrated blood pressure value, a single pulse wave propagation time measured for calibration, and the prestored constant α;

second operation means for calculating the blood pressure value from the pulse wave propagation time measured at a predetermined time interval for measuring a circadian blood pressure fluctuation, the constant α, and the constant β;

memory for consecutively storing the measured pulse wave propagation time and the blood pressure value calculated from the pulse wave propagation time; and output means for outputting at least one of the blood pressure value and pulse wave propagation time data stored in the memory as a result of the circadian blood pressure fluctuation measurement.

2. The blood pressure measuring apparatus as recited in claim 1 wherein, the time interval detection reference point detection means includes an electrode to be attached to a subject, and an electrocardiographic R wave detection section to which the electrode is connected.

3. The blood pressure measuring apparatus as recited in claim 1 wherein, the time interval detection reference point detection means includes a pulse wave detection section connected to at least one of a photoelectric pulse wave sensor and a pressure pulse wave sensor.

4. A blood pressure measuring method comprising the steps of:

storing a first constant by which a pulse wave propagation time is multiplied in calculating a blood pressure value from the pulse wave propagation time;

inputting a blood pressure value of a subject for calibration;

detecting a time interval detection reference point in a pulse wave on a side of an aortae of a living organism;

detecting a pulse wave on a side of peripheral blood vessels appearing with a time lag with respect to the pulse wave on the side of the aortae;

measuring a pulse wave propagation time based on respective detected outputs from the time interval detection reference point and the pulse wave on the side of the peripheral blood vessels appearing with a time lag with respect to the pulse wave on the side of the aortae;

determining a second constant to be used in calculating the blood pressure value from the pulse wave propagation time using the blood pressure value input for calibration., a single pulse wave propagation time measured for calibration, and the prestored first constant;

calculating the blood pressure value from the pulse wave propagation time measured at a predetermined time interval for measuring a circadian blood pressure fluctuation, the stored first constant, and the already determined second constant;

consecutively storing the measured pulse wave propagation time and the blood pressure value calculated from the pulse wave propagation time; and outputting at least one of the blood pressure value and pulse wave propagation time data stored in the memory as a result of the circadian blood pressure fluctuation measurement.

5. A blood pressure measuring apparatus comprising:

an input means for inputting a blood pressure value for calibration;

time interval detection reference point detection means for detecting a time interval detection reference point in a pulse wave on a side of an aortae of a living organism;

pulse wave detection means for detecting a pulse wave on a side of peripheral blood vessels appearing with a time lag with respect to the pulse wave on the side of the aortae;

pulse wave propagation time measurement section for measuring a pulse wave propagation time based on respective detected outputs from the time interval detection reference point detection means and the pulse wave detection means;

first operation means for determining a constant $\beta$ to be added in calculating the blood pressure value from the pulse wave propagation time using the inputted calibrated blood pressure value, a single pulse wave propagation time measured for calibration, and a constant $\alpha$;

second operation means for calculating the blood pressure value from the pulse wave propagation time measured at a predetermined time interval for measuring a circadian blood pressure, fluctuation, the constant $\alpha$, and the constant $\beta$;

memory for consecutively storing the measured pulse wave propagation time and the blood pressure value calculated from the pulse wave propagation time; and output means for outputting at least one of the blood pressure value and pulse wave propagation time data stored in the memory as a result of the circadian blood pressure fluctuation measurement, wherein the improvement comprises:

a memory for storing said constant $\alpha$ by which a pulse wave propagation time is multiplied in calculating a blood pressure value from the pulse wave propagation time.

6. A blood pressure measuring method comprising the steps of:

inputting a blood pressure value of a subject for calibration;

detecting a time interval detection reference point in a pulse wave on a side of an aortae of a living organism;

detecting a pulse wave on a side of peripheral blood vessels appearing with a time lag with respect to the pulse wave on the side of the aortae;

measuring a pulse wave propagation time based on respective detected outputs from the time interval detection reference point and the pulse wave on the side of the peripheral blood vessels appearing with a time lag with respect to the pulse wave on the side of the aortae;

determining a second constant to be used in calculating the blood pressure value from the pulse wave propagation time using the inputted blood pressure value for calibration, a single pulse wave propagation time measured for calibration, and a first constant;

calculating the blood pressure value from the pulse wave propagation time measured at a predetermined time interval for measuring a circadian blood pressure fluctuation, the first constant, and the previously determined second constant;

consecutively storing the measured pulse wave propagation time and the blood pressure value calculated from the pulse wave propagation time; and outputting at least one of the blood pressure value and the pulse wave propagation time data stored in the memory as a result of the circadian blood pressure fluctuation measurement, wherein the improvement comprises:

prior to the step of inputting a blood pressure value of a subject for calibration, storing the first constant by which the pulse wave propagation time is multiplied in calculating the blood pressure value from the pulse wave propagation time.

* * * * *